United States Patent [19]

Kresheck et al.

[11] Patent Number: 5,625,053

[45] Date of Patent: Apr. 29, 1997

[54] METHOD OF ISOLATING PURIFIED PLASMID DNA USING A NONIONIC DETERGENT, SOLUTION

[75] Inventors: Gordon C. Kresheck; Mitchell Altschuler, both of DeKalb, Ill.

[73] Assignee: Board of Regents For Northern Illinois Univ., DeKalb, Ill.

[21] Appl. No.: 296,812

[22] Filed: Aug. 26, 1994

[51] Int. Cl.$^6$ ..................... C07H 1/06
[52] U.S. Cl. ............ 536/25.41; 536/25.4; 210/634; 210/638; 210/511
[58] Field of Search ................ 210/634, 638, 210/511; 536/25.4, 25.41

[56] References Cited

U.S. PATENT DOCUMENTS 5,271,840 12/1993 Kresheck ................ 210/634

OTHER PUBLICATIONS

Maniatis, Molecular Cloning, A Laboratory Manual, pp. 90–91, (1982).

Primary Examiner—James O. Wilson
Attorney, Agent, or Firm—Wood, Phillips, VanSanten, Clark & Mortimer

[57] ABSTRACT

A method of isolating purified plasmid DNA includes the steps of providing cells containing plasmid DNA and lysing the cells with an alkyldimethylphosphine oxide (APO) detergent to produce a mixture, centrifuging the cell and APO mixture, reserving a supernatant containing purified plasmid DNA and isolating the purified plasmid DNA, from the supernatant. Isolation and purification occurs in the absence of hazardous materials such as phenol and chloroform. Prior to mixing, the APO detergent is preferably combined with a strong base to produce a stable solution.

15 Claims, 3 Drawing Sheets

METHOD OF ISOLATING PURIFIED PLASMID DNA USING A NONIONIC DETERGENT, SOLUTION

TECHNICAL FIELD

This invention generally relates to the isolation of purified plasmid deoxyribose nucleic acid (DNA). More particularly, the invention relates to a method of isolating purified plasmid DNA using an alkyldimethylphosphine oxide (APO) detergent, a solution containing the APO detergent, and a kit containing the APO detergent.

BACKGROUND OF THE INVENTION

Plasmid deoxyribose nucleic acid (DNA) is a circular or looped format of genetic material located within all living cells. Purified plasmid DNA is widely studied and exploited in molecular biology as a tool to determine gene structure and function. One use of the purified plasmid DNA is the mapping of the human genome. The purified plasmid DNA must be sufficiently pure so as to permit additional investigational manipulations involving restriction enzymes and sequencing.

Two procedures to isolate plasmid DNA are alkaline lysis (Maniatis et al., *Molecular Cloning: A Laboratory Manual*, 2d ed., Cold Spring Harbor Laboratory, Cold Spring Harbor, N.Y. (1989)) and boiling (Akela et al, *Rapid Isolation and Sequencing of Double Stranded Plasmid DNA*, Biotechniques 14: 726–728 (1993) and Holmes et al., *A Rapid Boiling Method for the Preparation of Bacterial Plasmids*, Anal. Biochem. 114: 193–197 (1981)). Many of these methods use hazardous chemicals such as phenol/chloroform, guanidine hydrochloride and the like. Detergents used in these procedures often contain a phenyl ring that interferes with ultraviolet (UV) spectrophotometric analysis of proteins or nucleic acids. Some detergents, such as sodium dodecylsulfate (SDS), leave a residue that inhibits cutting of the plasmid DNA with restriction enzymes.

Reduction or elimination of phenol in the preparation of isolated plasmid DNA is highly desirable. Wang et al, *Simplified Large-Scale Alkaline Lysis Preparation of Plasmid DNA With Minimal Use of Phenol*, Biotechniques, Vol. 17, No. 1, pp 27–28 (1994).

Holmes et at. discloses a boiling method for plasmid isolation that uses Triton X-100. Triton X-100 has the following shortcomings:

(a) Due to a phenyl ring in its structure, Triton X-100 interferes with direct, spectral estimations of protein and nucleic acid concentration.

(b) Triton X-100 is not a definable, pure compound. Rather, it is a mixture containing various chain lengths of ethoxylated isooctylphenol. The use of undefined mixtures is not compatible with Good Manufacturing Practice (GMP) procedures often required for processing of pharmaceuticals.

(c) Polyethoxylated nonionic detergents such as Triton X-100 frequently are contaminated or become contaminated with peroxides upon aging. This contaminant can be especially destructive to the biological integrity and activity of proteins and nucleic acids.

(d) In order to maintain solutions of Triton X-100 above the cloud point of 30° C., external heat must be continuously applied which adds mechanical complexity and further increases the risk of damaging certain sensitive proteins and nucleic acids.

During isolation of plasmid DNA from bacteria, a large number of double stranded DNA templates are routinely generated. Some of the DNA templates contain significant amounts of secondary structures that often terminate the sequencing reactions prematurely making it difficult to read and analyze the DNA. One way to overcome this problem is to sub-clone the DNA fragment into a single stranded vector such as M13. Alternately, high temperature sequencing can be performed using, e.g., Taq polymerase. However, high temperature sequencing has been shown to be prone to error. See, for example, Lee-Jackson et al., *Artifactual Frame Shift p53 Mutation at Codon 249 Detected with Cyclyst™ DNA Sequencing Method*, Biotechniques 15: 363–4 (1993).

Many detergents such as SDS that include an ester undergo alkaline hydrolysis that makes them unstable in alkaline solutions such as those produced by mixing SDS and sodium hydroxide. Due to this lack of stability, the sodium hydroxide and SDS solution should be made fresh before every use which renders alkaline SDS solutions useless for inclusion in a kit to isolate purified plasmid DNA. See Wang et al.

A method of isolating purified plasmid DNA, solution and kit that overcome at least some of the above-identified shortcomings is highly desirable.

SUMMARY OF THE INVENTION

A method of isolating purified plasmid deoxyribose nucleic acid (DNA) includes the steps of providing cells containing plasmid DNA and mixing the cells with an alkyldimethylphosphine oxide (APO) detergent. The method can also include the step of isolating purified plasmid DNA from the whole cell and APO detergent mixture. The method is performed in the absence of hazardous chemicals typically used in other, conventional isolation and purification methods.

The APO detergent does not interfere with the UV spectrophotometric analysis of proteins or nucleic acids. This lack of interference is presently theorized to be due to the lack of a phenyl ring in the APO detergent. Residual APO detergent causes less inhibition of cutting of the DNA with restriction enzymes as compared to residual sodium dodecylsulfate (SDS).

The APO detergent is a definable, substantially pure compound that makes it compatible with Good Manufacturing Practice (GMP) procedures often required for processing of pharmaceuticals. The APO detergent is not contaminated nor does it become contaminated with peroxides upon aging which avoids the problems associated with loss of biological integrity or activity often seen when contaminants are present in other detergents. External heat need not be continuously applied which minimizes mechanical complexity and reducing the risk of damaging certain sensitive proteins and nucleic acids.

There is little or no premature termination during sequencing reactions using DNA isolated with APO detergent, which results in improved reading and analysis of DNA sequencing. The improved results are presently theorized to be due to the effect of APO detergent on secondary structures. The elimination of the problem with secondary structures means that there is no need to sub-clone the DNA fragment into a single stranded vector or use high temperature sequencing.

The APO detergent is stable in an alkaline solution, and it does not undergo alkaline hydrolysis. This makes the APO detergent-containing alkaline solution suitable for use in a kit. A novel method of using the APO detergent includes the step of combining the APO detergent with whole cells containing plasmid DNA to lysis the cells.

A stable solution includes the APO detergent and sodium hydroxide.

A kit for isolating plasmid DNA includes the APO detergent and can include the APO detergent mixed with sodium hydroxide.

Numerous other advantages and features of the present invention will become readily apparent from the following detailed description of the preferred embodiments and the appended claims.

DETAILED DESCRIPTION OF THE PREFERRED EMBODIMENT

Although this invention is susceptible to embodiment in many different forms, there are described in detail herein, presently preferred embodiments of the invention. It should be understood, however, that the present disclosure is to be considered as an exemplification of the principles of this invention and is not intended to limit the invention to the embodiments described.

A method of isolating purified plasmid deoxyribose nucleic acid (DNA) includes the steps of providing cells containing plasmid DNA and mixing the cells with an alkyldimethylphosphine oxide (APO) detergent. The method isolates and purifies DNA from the mixture in the absence of hazardous chemicals such as phenol and chloroform. A representative procedure for isolating and purifying is an alkaline lysis procedure, which is preferred and described in more detail herein below. Alternatively, lysis can be performed by a boiling procedure that uses a nonionic detergent, e.g., Triton X-100. In both procedures, the APO detergent is substituted for the conventional detergent.

Figure 1:
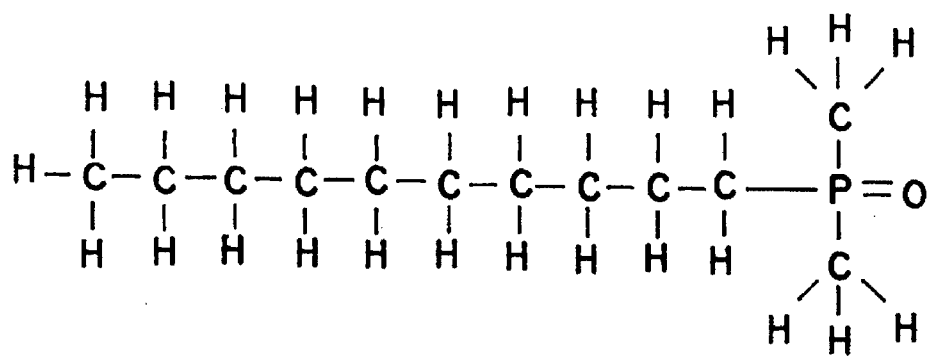
FIG. 1 illustrates the structure of a preferred alkyldimethylphosphine oxide detergent (APO-10)
Figure 2:
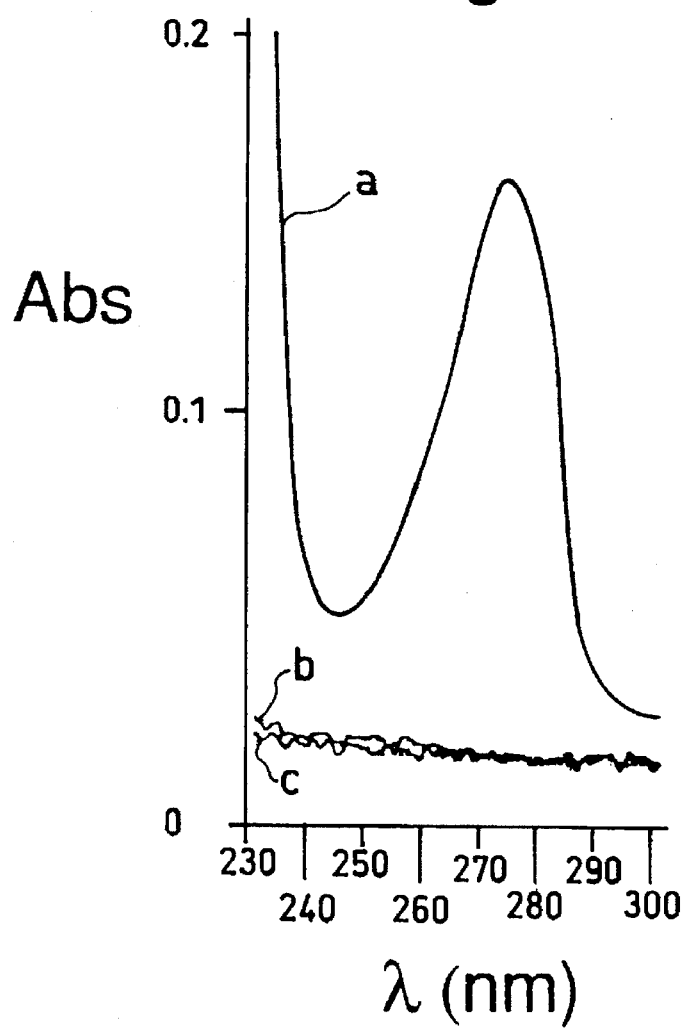
FIG. 2 is a comparison of the ultra-violet (UV) absorption spectra of a 0.1 mM Triton® X-100 solution (a), a 1.0 mM APO-10 solution (b) and water (c) between 230 and 300 nanometers.

The APO detergent is a substituted aliphatic alkane nonionic detergent having the following formula:

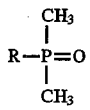

wherein R is a straight chain saturated alkyl moiety having about 6 to about 24, preferably about 8 to about 14, carbon atoms. The most preferred APO detergents are decyldimethylphosphine oxide (APO-10) and dodecyldimethylphosphine oxide (APO-12). FIG. 1 illustrates the structure of APO-10. FIG. 2 illustrates the ultra-violet (UV) absorption spectrum of a 1.0 mM APO-10 solution (b) as compared to a 0.1 mM Triton® X-100 solution (a) and water (c). The full scale of FIG. 2 corresponds to 0.2 absorbance units.

The APO detergents are preferably synthesized by the method described in Laughlin, *Journal of Organic Chemistry*, Vol. 30, pp 1322–1324 (1965) and Hays, *Journal of Organic Chemistry*, Vol. 33, pp. 3690–94 (1968). The APO detergent is also commercially available.

The cell can be obtained from a bacteria, mammalian, yeast or similar source. Representative bacteria include *Eschericheria coli, Bacillus subtilis, Agrobacterium tumefaciens* and the like. Representative mammalian tissues or cells include those known to be useful for DNA research. A representative yeast cell is Saccharomyces cerevisiae.

For the alkaline lysis procedure, the cells and APO detergent are mixed under conditions to lyse the cells. Preferably, the conditions include a temperature in the range of about 0° to about 25° C., a time period of about 10 to about 30 minutes and adequate agitation.

The cells are grown in a suitable growth medium, harvested using a centrifuge and the resulting pellet subsequently resuspended in a buffer prior to mixing of the cells with the APO detergent. The APO detergent can be introduced into the resuspension as a solution or a solid. The mixture is neutralized and centrifuged to obtain a supernatant that is then precipitated. The precipitated supernatant is centrifuged to produce a pellet of plasmid DNA that is washed with an alcohol to effect extraction of the purified DNA and then dried to produce a pellet of isolated and purified DNA. Water or the buffer containing a hydrolytic agent can be used to remove any residual RNA from the DNA pellet. The resulting DNA is ready for either restriction digestion or double stranded DNA sequencing. The cell-containing growth medium, mixture and precipitated supernatant are centrifuged under conditions effective to obtain the pellet or supernatant. The growth medium, buffer and neutralizing agent are convention and are selected based on the cell being used as one of ordinary skill in the art recognizes.

The buffer is preferably a solution containing 50 mM glucose, 10 mM ethylene-diaminotetra-acetic acid (EDTA) and 25 mM tris (hydroxymethyl) amino methanol (Tris). The buffer has a pH of about 8.0.

The APO detergent is preferably used with a strong base, e.g., sodium hydroxide, potassium hydroxide or the like. The APO detergent is preferably present an amount in the range of about 0.5 to about 5 weight percent (wt %). The hydroxide is preferably present in an amount in the range of about 0.5 to about 5 wt %. The weight percents are based on the total weight of the mixture of the APO detergent, hydroxide and water.

Alternatively, the APO detergent can be in a solid state mixed with the cells.

The neutralizing agent is preferably a 3M potassium acetate solution having a pH of about 4.8.

Preferably, the precipitating and extracting steps are performed using a lower alcohol, e.g., methanol, ethanol or propanol. The extracting step can be performed using a solution containing about 60 to about 80 volume percent of the alcohol and 20 to 40 volume percent of water or an appropriate buffer.

The hydrolytic agent that is mixed with water or the buffer to remove any residual RNA is preferably RNase A.

The APO detergent and sodium hydroxide solution is very stable for prolonged time periods, has a long shelf life and shows no signs of chemical decomposition when stored at room temperature for prolonged time periods. Ongoing testing of a 1% APO-10 in 0.2N sodium hydroxide solution at room temperature shows no change in the proton and phosphorus $^{31}$P NMR spectra after six weeks. The stability makes the APO detergent and the solution containing the APO detergent very desirable as part of a kit to isolate and purify plasmid DNA. The kit can also contain other reagents and the like used to isolate and purify the DNA. These other reagents include buffers, neutralizers, precipitating agents, washes, and the like.

A method of using the APO detergent includes the step of combining the APO detergent with whole cells containing plasmid DNA to lyse the cells. Preferably, the APO detergent is combined with sodium hydroxide.

The following examples are given by way of representation and not limitation.

EXAMPLE 1: ISOLATION OF PURIFIED PLASMID DNA

To isolate plasmid DNA, *E. coli* bacteria (DH5α) was briefly spun down (1 min in a microfuge) after an overnight growth in Circlegrow™ (Bio 101) containing the antibiotic ampicillin (100 µg per ml). The supernatant was discarded and the pellet retained. To the pellet, 100 µl of Solution I (50 mM glucose, 10 mM EDTA and 25 mM Tris, pH 8.0), 200 µl of Solution II (0.2N sodium hydroxide, 1% APO-10), and 150 µl of Solution III (3M potassium acetate, pH 4.8) were added sequentially at five-minute intervals to produce a sample. The APO-10 was obtained from Pierce Chemical Co., Rockford, Ill. Solution I is a buffer that resuspends the pellet, Solution II lysis the cell and Solution III neutralizes the base, i.e., the sodium hydroxide, in preparation for the next step. The sample was centrifuged for 15 minutes at 4° C. in a microfuge, the pellet discarded and the supernatant precipitated with 1 ml of 100% ethanol for 5–10 minutes. The precipitated supernatant was then centrifuged for 15 minutes at 4° C. in a microfuge, the supernatant discarded, the pellet washed with 500 µl of 70% ethanol and then dried to produce isolated, purified plasmid DNA. The plasmid DNA was then brought up in 25 µl of water or TE (10 mM Tris, 1 mM EDTA, pH 8) with 1 µl of 10 mg/ml RNase A (Sigma). The isolated plasmid DNA is ready for either restriction digestion or double stranded DNA sequencing.

EXAMPLE 2: COMPARISON OF PROCEDURES AND YIELDS

The plasmid digestion and/or double strand sequencing of DNA isolated using APO-10 (Procedure A—described above in EXAMPLE 1) and of DNA isolated using two other techniques (Procedures B and C) were compared. Procedure B differed from Procedure A only in that 1% SDS was substituted for the 1% APO-10 in Solution II. Procedure C was similar to Procedure B except that the supernatant was extracted sequentially with phenol and chloroform instead of 70% ethanol. For the sequential extraction, an equal volume of phenol was added to the supernatant, the tube vortexed and centrifuged for five minutes in a microfuge at room temperature. To extract the top phase, an equal amount of chloroform was added with the resultant mixture being vortexed, centrifuged and the DNA of the aqueous phase precipitated with 1 ml of ethanol. The precipitated DNA was centrifuged for 15 minutes in a microfuge at 4° C., washed and respun. The pellet was brought up in 25 µl of TE and 1 µl of RNase A (10 mg/ml).

The yields of DNA isolated by Procedures A, B and C were found to be nearly identical (within about 3%) based on absorbance readings at 260 nm. The relative yield of isolated DNA was determined by a florescence technique using the preferred binding of Hoechst Dye 33258 (bis Benzimide) to DNA. The yield of DNA isolated by Procedures A, B and C were very similar (within about 7%).

EXAMPLE 3: DETERMINATION OF THE EFFECT OF APO DETERGENT ON DNA DIGESTION

Figure 3:
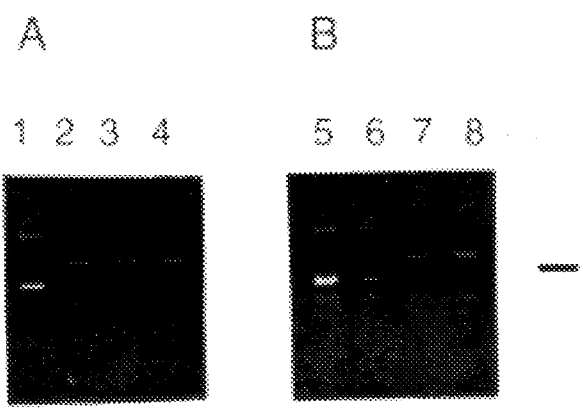
FIG. 3 illustrates DNA isolated using APO-10 in lanes 1, 2, 3 and 4 and using SDS, no phenol, lanes 5, 6, 7 and 8.

The digestion of DNA isolated using Procedure A was compared with the digestion of DNA isolated using Procedure B. Restriction was accomplished using one unit of the restriction enzyme Pst 1 per 0.5 µg of isolated DNA for various lengths of time. Referring to FIG. 3, lanes 1, 2, 3 and 4 are for DNA isolated using Procedure A and lanes 5, 6, 7 and 8 are for DNA isolated using Procedure B. The lengths of time are as follows: zero minutes for lanes 1 and 5; one minute for lanes 2 and 6; five minutes for lanes 3 and 7; and 30 minutes for lanes 4 and 8. After one minute, the DNA isolated by Procedure A was almost entirely converted into a linear form (see FIG. 3, lane 2). In contrast, the plasmid isolated by Procedure B is not linear at a time period of up to five minutes later (see FIG. 3, lane 7). These results indicate that either the APO isolation yields a cleaner preparation or that residual APO detergent causes less inhibition of the restriction digest than residual SDS. In FIG. 3, the line marks the linear form.

EXAMPLE 4: DETERMINATION OF THE EFFECT OF APO DETERGENT ON DNA SEQUENCING

Figure 4:
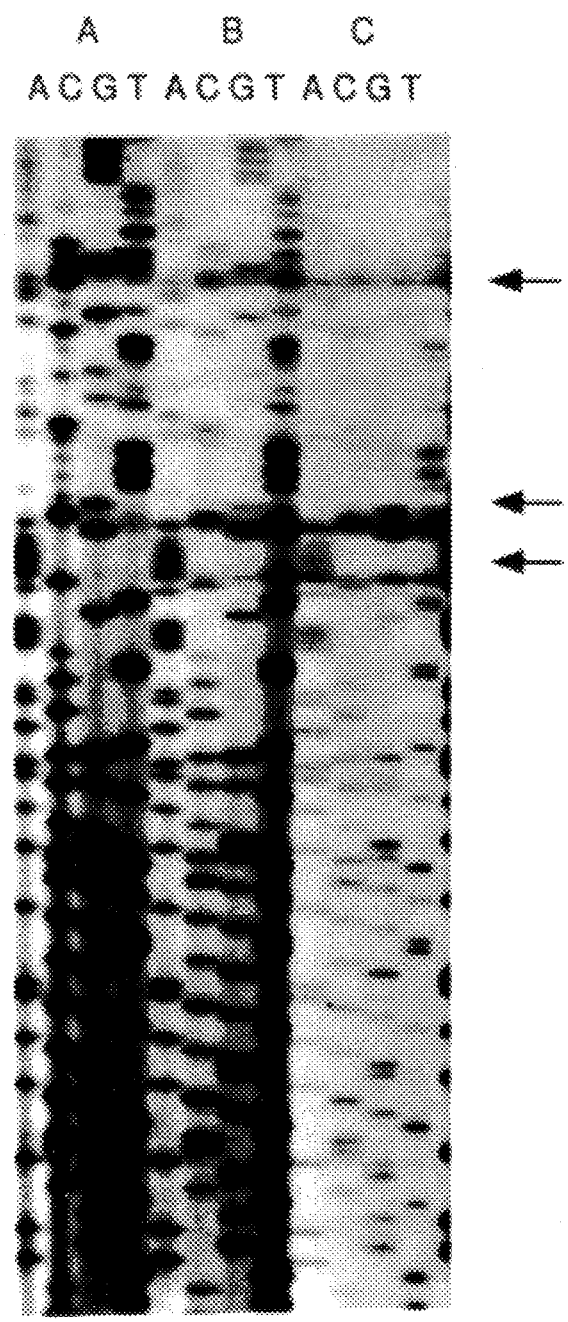
FIG. 4 illustrates the sequence of plasmid DNA illustrated using APO-10 (A), SDS without phenol/chloroform (B) and SDS with phenol/chloroform (C).

To test the relative ability of DNA isolated by each of the three procedures to be sequenced, a plasmid containing a plant lipoxygenase gene, which has significant problems with premature termination (Altschuler, unpublished), was used. For this comparison, an equal volume (2.5 µl) of DNA solution from individually isolated plasmid using Procedures A, B and C was subjected to denaturation and annealed with a T7 primer (see, for example, Barker, *A More Robust, Rapid Alkaline Denaturation Sequencing Method,* Biotechniques 14: 168–70 (1993). Samples (2.5 µl) were heated to 65° C. for 10 minutes prior to adding 7 µl of NSA buffer, i.e., 400 mM Tris-HCl, pH 7.5, 200 mM $MgCl_2$, followed by returning the samples to a temperature of 65° C. for 10 minutes. The samples were permitted to cool to room temperature and then sequenced using the sequenase enzyme kit suggested by the manufacturer (USB, Cleveland, Ohio) with the following differences: a mixture was made for eight sets of reactions that included 16 µl of diluted labeling mix, 8 µl (0.1M) DTT, 4 µl $P^{32}$ dATP, 13 µl Enzyme dilution buffer, 1 µl Pyrophosphatase and 2 µl Sequenase. To each sample, 5.4 µl of this mixture was introduced. After an incubation of five minutes at room temperature, 3.5 µl of the labeling reactant was introduced into four tubes, each containing 2.5 µl of the appropriate termination mixture containing the appropriate dideoxyribonucleotides. The samples were centrifuged, resuspended by shaking, centrifuged again and incubated at 37° C. for five minutes. Then, 3.5 µl of dye was added to each tube following by heating to 65° for 15 minutes before 3 µl of each reaction product was loaded and analyzed on a 7% polyacrylamide gel. As can be seen in FIG. 4, the DNA isolated by Procedures A, B and C are suitable templates for DNA sequencing. However, due to the enhanced efficiency of the polymerization step in the sequencing of the sample isolated by Procedure A, the sequencing band intensity was greatest for DNA isolated by Procedure A in a relative short period of time. When the gel is exposed to reveal sequential information for Procedures B and C, sequence information using Procedure A looks overexposed which again shows the superiority of Procedure A. In FIG. 4, termination regions are designated by A, C, G and T. Regions of premature sequencing termination are marked with a line.

Of equal interest is when domains of high secondary sequence are analyzed. In this case, all treatments that utilize SDS (Procedures B and C) result in a significant amount of premature termination during the extension reaction. In contrast, the isolation Procedure A (which includes APO-10) did not result in significant premature termination.

The use of the APO detergent produces isolated plasmid DNA that is more amenable to cutting with restriction enzymes. The use of APO detergent in DNA sequencing greatly reduces any problems in reading sequences that have secondary structures. The use of the APO detergent improves the speed of obtaining the DNA, lowers the cost of the method and advantageously permits sequence of DNA sequences with strong secondary structures which increase the cutting ability of the restriction enzymes and generates DNA templates that have less secondary structure problems with respect to sequencing. The use of the APO detergent to DNA isolation decreases the cost, time and effort needed to isolate clean DNA template for DNA manipulation, especially sequencing. These advantages are of great importance to projects that analyze large numbers of DNA sequences such as the human genome project.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the an will appreciate.

We claim:

1. A method of isolating purified plasmid DNA comprising the steps of:

providing cells containing plasmid DNA;

lysing the cells with an alkyldimethylphosphine oxide (APO) detergent in the presence of a strong base and solubilizing the plasmid DNA, to produce a mixture;

centrifuging the cell and APO mixture to obtain a supernatant containing the plasmid DNA; and isolating purified plasmid DNA from the supernatant.

2. The method of claim 1 wherein the alkyl moiety of the APO detergent is a straight, saturated aliphatic carbon chain containing about 6 to about 24 carbon atoms.

3. The method of claim 1 wherein the alkyl moiety of the APO detergent is a straight, saturated aliphatic carbon chain containing about 8 to about 14 carbon atoms.

4. The method of claim 1 wherein the APO detergent is selected from the group consisting of decyldimethylphosphine oxide and dodecyldimethylphosphine oxide.

5. The method of claim 1 further comprising the step of isolating the purified DNA from the mixture in the absence of hazardous materials.

6. The method of claim 1 further comprising the step of combining the APO detergent with a strong base.

7. The method of claim 6 wherein the strong base is selected from the group consisting of sodium hydroxide and potassium hydroxide.

8. The method of claim 1 wherein the step of isolating purified plasmid DNA is performed by precipitating the DNA from the supernatant.

9. The method of claim 8 further comprising the step of extracting the DNA, the extracting step being performed after the precipitating step.

10. The method of claim 9 wherein the precipitating and extracting steps are alcohol precipitating and extracting steps.

11. A method of isolating purified plasmid DNA comprising the steps of:

providing cells containing plasmid DNA;

forming a pellet by centrifuging the cells and removing the pellet from a supernatant;

resuspending the pellet in a buffer solution at a pH in a basic range;

lysing the cells in the buffer solution using an alkyldimethylphosphine oxide (APO) detergent;

centrifuging the solution to obtain a supernatant containing the plasmid DNA;

precipitating the purified plasmid DNA from the supernatant.

12. A stabile solution comprising an alkyldimethylphosphine oxide (APO) detergent in an amount in the range of about 0.5 to about 5 weight percent, a strong base in an amount in the range of about 0.5 to about 5 weight percent and a solvent.

13. The solution of claim 12 wherein the strong base is selected from the group consisting of sodium hydroxide and potassium hydroxide.

14. A kit for isolation of plasmid DNA comprising an alkyldimethylphosphine oxide (APO) detergent in a solution in an amount in the range of about 0.5 to 5 weight percent combined with a strong base in an amount sufficient to bring the solution into a basic range, and a solvent.

15. The method of claim 11 wherein the step of precipitating purified plasmid DNA is performed using a low alcohol selected from the group comprising, methanol, ethanol or propanol.

* * * * *